(12) United States Patent
Smolyaninov et al.

(10) Patent No.: US 7,362,440 B2
(45) Date of Patent: Apr. 22, 2008

(54) FAR-FIELD OPTICAL MICROSCOPE WITH A NANOMETER-SCALE RESOLUTION BASED ON THE IN-PLANE IMAGE MAGNIFICATION BY SURFACE PLASMON POLARITIONS

(75) Inventors: Igor I. Smolyaninov, Columbia, MD (US); Christopher C. Davis, Bowie, MD (US)

(73) Assignee: The University of Maryland, Riverdale, MD (US)

( * ) Notice: Subject to any disclaimer, the term of this patent is extended or adjusted under 35 U.S.C. 154(b) by 184 days.

(21) Appl. No.: 11/256,853

(22) Filed: Oct. 24, 2005

(65) Prior Publication Data
US 2007/0229835 A1 Oct. 4, 2007

Related U.S. Application Data

(63) Continuation of application No. 11/061,837, filed on Feb. 18, 2005.

(60) Provisional application No. 60/546,146, filed on Feb. 20, 2004, provisional application No. 60/569,305, filed on May 7, 2004.

(51) Int. Cl.
*G01N 21/55* (2006.01)
(52) U.S. Cl. .................. 356/445; 356/446
(58) Field of Classification Search ......... 356/445–446
See application file for complete search history.

(56) References Cited

U.S. PATENT DOCUMENTS

2005/0185186 A1* 8/2005 Smolyaninov et al. ...... 356/445

* cited by examiner

*Primary Examiner*—Gregory J. Toatley, Jr.
*Assistant Examiner*—Tri Ton
(74) *Attorney, Agent, or Firm*—Carter, DeLuca, Farrell & Schmidt, LLP

(57) ABSTRACT

A far-field optical microscope capable of reaching nanometer-scale resolution using the in-plane image magnification by surface plasmon polaritons is presented. The microscope utilizes a microscopy technique based on the optical properties of a metal-dielectric interface that may, in principle, provide extremely large values of the effective refractive index $n_{eff}$ up to $10^2$-$10^3$ as seen by the surface plasmons. Thus, the theoretical diffraction limit on resolution becomes $\lambda/2n_{eff}$, and falls into the nanometer-scale range. The experimental realization of the microscope has demonstrated the optical resolution better than 50 nm for 502 nm illumination wavelength.

9 Claims, 10 Drawing Sheets

FAR-FIELD OPTICAL MICROSCOPE WITH A NANOMETER-SCALE RESOLUTION BASED ON THE IN-PLANE IMAGE MAGNIFICATION BY SURFACE PLASMON POLARITIONS

PRIORITY

This application is a continuation application of an application filed on Feb. 18, 2005 and assigned U.S. application Ser. No. 11/061,837 which claims priority under 35 U.S.C. §119(e) to a U.S. Provisional Application filed on Feb. 20, 2004 and assigned U.S. Provisional Application No. 60/546,146 and to a U.S. Provisional Application filed on May 7, 2004 and assigned U.S. Provisional Application No. 60/569,305. The contents of all priority applications are incorporated herein by reference.

STATEMENT REGARDING FEDERALLY SPONSORED RESEARCH

This invention was made with government support under NSF contract nos. ECS-0210438 and ECS-0304046 awarded by the National Science Foundation. The government has certain rights in this invention.

BACKGROUND OF THE INVENTION

1. Technical Field

The disclosure relates to optical microscopy. In particular, the disclosure relates to a far-field optical microscope with a nanometer-scale resolution based on the in-plane image magnification by surface plasmon polaritons.

2. Description of the Prior Art

Far-field optical microscopy remains invaluable in many fields of science, even though various electron and scanning probe microscopes have long surpassed it in resolving power. The main advantages of the far-field optical microscope are the ease of operation and direct sample visualization. Unfortunately, the resolution of a regular optical microscope is limited by the wavelength of visible light. The reason for the limited resolution is diffraction and, ultimately, the uncertainty principle: a wave can not be localized much tighter than half of its vacuum wavelength $\lambda/2$.

Immersion microscopes introduced by Ernst Abbe in the 19th century have slightly improved resolution on the order of $\lambda/2n$ because of the shorter wavelength of light $\lambda/n$ in a medium with refractive index n. However, immersion microscopes are limited by the small range of refractive indices n of available transparent materials. It was believed that the only way to achieve nanometer-scale spatial resolution in an optical microscope is to beat diffraction, and detect evanescent optical waves in very close proximity to a studied sample using a scanning near-field optical microscope. Although many fascinating results are obtained with near-field optics, such microscopes are not as versatile and convenient to use as regular far-field optical microscopes. For example, an image of a near-field optical microscope is obtained by point-by-point scanning, which is an indirect and a rather slow process.

However, it has been realized that a dielectric droplet on a metal surface which supports propagation of surface plasmons (or surface plasmon polaritons) may have an extremely large effective refractive index as seen by these modes (see I. I. Smolyaninov, Surface plasmon toy-model of a rotating black hole, *New Journal of Physics*, vol. 5, pages 147.1-147.8, October 2003, the contents of which are incorporated herein by reference). The properties of surface plasmons and convenient ways to excite them are described in detail in H. Raether, *Surface Plasmons*, Springer Tracts in Modern Physics, vol. 111, Springer, Berlin, 1988.

Accordingly, it is an aspect of the present disclosure to describe a far-field optical microscope capable of reaching nanometer-scale resolution using the in-plane image magnification by surface plasmon polaritons based on the optical properties of a metal-dielectric interface that may provide extremely large values of the effective refractive index $n_{eff}$ up to $10^3$ as seen by surface polaritons, and thus the diffraction limited resolution can reach nanometer-scale values.

SUMMARY OF THE INVENTION

The present disclosure describes a far-field optical microscope capable of reaching nanometer-scale resolution using the in-plane image magnification by surface plasmon polaritons, also known as two-dimensional light, which is made of electromagnetic waves coupled with conducting electrons. The immersion microscope of the present disclosure improves resolution using an approach based on the optical properties of a metal-dielectric interface that may provide extremely large values of the effective refractive index $n_{eff}$ up to $10^3$ as seen by surface polaritons. Thus, the diffraction limited resolution can reach nanometer-scale values of $\lambda/2 \, n_{eff}$. The experimental realization of such an immersion microscope has demonstrated the optical resolution better than 50 nm at 502 nm illumination wavelength.

The microscopy technique employed by the immersion microscope of the present disclosure improves resolution without expensive equipment and special preparations needed for electron microscopes and other technologies. The microscopy technique entails coaxing plasmon polaritons into magnifying images by placing a microscopic sample onto a thin, coated glass surface (such as a meta-coated glass surface that supports propagation of surface electromagnetic waves), like a document on the surface of a photocopier, and depositing a drop of glycerin or other substance on top of it. Alternatively, instead of depositing a drop of glycerin or other substance, a solid parabolically shaped dielectric layer can be provided on the metal surface. Laser light is then propagated or shined through the glass creating surface plasmon polaritons in the metal-coating. The plasmon polaritons "sense" the sample by scattering off of it. They can sense finer details than ordinary light because their wavelength is only 70 nm, seven times shorter than that of the laser.

To concentrate the scattered two-dimensional light, the curved vertical surface of the glycerin drop where the light contacts the metallic plane and reflects plasmon polaritons is used. This vertical surface (metal-dielectric interface) works a bit like a giant radio telescope dish in reverse: rather than focusing parallel astronomical light rays to a point, it collects the scattered plasmon polaritons emerging from the sample and redirects them as a plasmon beam along the metallic plane. To view the image, nanoscale irregularities in the metal surface scatter some of the light of the beam upward, so that an ordinary microscope objective can catch the image and be viewed through at least one lens of the microscope positioned for viewing the image propagated by the scattered beam. The droplet's shape is adjusted "by hand" using micromanipulators, such as a probe.

However, it should be noted that the term "focal point" does not only include structures that modify surface plasmon polaritons by directing them to a point, but rather it is intended to include properties of directing and/or modify the direction of travel of surface plasmon polaritons. For example, a droplet may include a focal point that is opposite to the direction of travel of the surface plasmon polaritons making the droplet behave, in analogy only, as a negative lens. Additionally or alternatively, a droplet and/or structure may include at least one focal point for changing the direction of travel of surface plasmon polaritons and that droplet and/or structure may behave, in analogy only and as mentioned supra, similar to a radio telescope dish in reverse; rather than focusing parallel surface plasmon polaritons "rays" to a point, it may collect the scattered plasmon polaritons emerging form the same and redirect them as a plasmon beam along the metallic plane. Also, a focal point may not actually be a "point" on the plane, but rather may include an area that may be regarded as a focal point having a value that is a function of arbitrary two-dimensional X and Y axis. Therefore, in some contexts herein, the mentioning of a device and/or structure having a "focal point" is to point out that the device and/or structure may be analogizes with ray optics.

BRIEF DESCRIPTION OF THE FIGURES

These and other advantages will become more apparent from the following detailed description of the various embodiments of the present disclosure with reference to the figures wherein:

FIG. 3(e) is a schematic illustrating how the mode coupling effect may conserve angular resolution;

DETAILED DESCRIPTION OF THE PREFERRED EMBODIMENTS

The present disclosure describes a far-field optical microscope capable of reaching nanometer-scale resolution using the in-plane image magnification by surface plasmon polaritons based on the optical properties of a metal-dielectric interface that may provide extremely large values of the effective refractive index $n_{eff}$ up to $10^3$ as seen by surface polaritons, and thus the diffraction limited resolution can reach nanometer-scale values.

I. Introduction

The wave vector of a surface plasmon propagating over an interface between a dielectric and an infinitely thick metal film is defined by the expression $$k_p = \frac{\omega}{c}\left(\frac{\varepsilon_d \varepsilon_m}{\varepsilon_d + \varepsilon_m}\right)^{1/2} \qquad (1)$$

where $\epsilon_m(\omega)$ and $\epsilon_d(\omega)$ are the frequency-dependent dielectric constants of the metal and dielectric, respectively. If the imaginary part of the metal's dielectric constant is neglected, under the resonant condition $$\epsilon_m(\omega) = -\epsilon_d(\omega) \qquad (2)$$

both phase and group velocities of the surface plasmons tend to zero. This means that the wavelength $\lambda_p$ of such plasmons becomes very small just below the optical frequency defined by equation (2), or in other words, the effective refractive index of the dielectric $n_{eff}$ becomes extremely large as seen by the propagating surface plasmons in this frequency range. As a result, a small droplet of liquid dielectric, e.g., glycerin, on the metal surface, e.g., gold film, becomes a very strong lens for surface plasmons propagating through the droplet from the outside. On the other hand, the droplet boundary becomes an extremely efficient mirror for surface plasmons propagating inside the droplet at almost any angle of incidence due to the total internal reflection (this leads to the "black hole" analogy described in I. I. Smolyaninov, Surface plasmon toy-model of a rotating black hole, *New Journal of Physics*, vol. 5, pages 147.1-147.8, October 2003).

II. Surface Plasmon Immersion Microscope

The above-described realization has led to the introduction of a surface plasmon immersion microscope 10 as described below with reference to the figures.

Figure 1A:
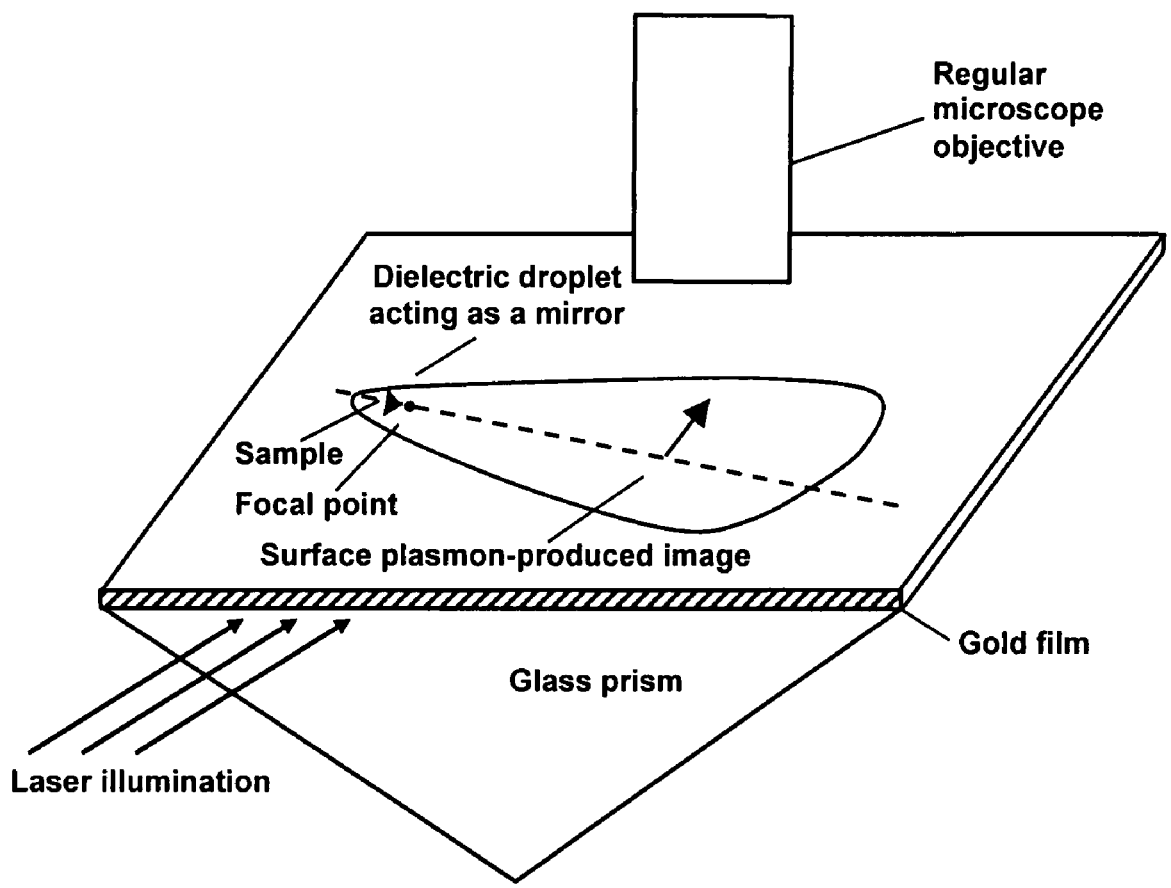
FIG. 1(a) is a schematic illustration of a surface plasmon immersion microscope where surface plasmons are excited by laser light and propagate inside a parabolic-shaped droplet and the placing of a sample near the focus of a parabola produces a magnified image in the metal plane in accordance with the present disclosure.

Let us consider a far-field two-dimensional optical microscope made of dielectric droplets 12 as shown in FIG. 1(a). Since the wavelength of surface plasmons $\lambda_p$ observed in the STM light emission (see I. I. Smolyaninov, V. S. Edelman, and V. V. Zavyalov, Spectroscopic measurements of light emitted by the STM, *Phys. Letters A*, vol. 158, pages 337-340, 1991) and near-field optical experiments (see H. J. Maas, J. Heimel, H. Fuchs, U. C. Fischer, J. C. Weeber, and A. Dereux, Photonic nanopatterns of gold nanostructures indicate the excitation of surface plasmon modes of a wavelength of 50-100 nm by scanning near-field optical microscopy, *Journal of Microscopy*, vol. 209, pages 241-248, 2002) may be as small as a few nanometers (hence $n_{eff} = \lambda/\lambda_p$ may reach extremely large values up to $10^2$), the diffraction limit of resolution of such a two-dimensional microscope may approach $\lambda_p/2$ or $\lambda/2\ n_{eff}$. Theoretically, it may reach a scale of a few nanometers.

If a sample 14 under investigation is forced to emit propagating surface plasmons using laser illumination 16, or if it is illuminated by propagating plasmons, these plasmons may produce a two-dimensional magnified image 18 of the sample 14 in the appropriate location on a metal surface 20 placed on a glass prism 22 or other similar optical device. The metal surface 20 as shown in FIG. 1(a) is a gold film. Other metallic and non-metallic coatings can be used to coat a top surface of the glass prism 22 in accordance with the present disclosure, such as silver, copper, aluminum, semiconductors, other types of metals, and other film material which supports surface electromagnetic wave propagation.

The adjective "magnified", such as when referring to a two-dimensional "magnified" image, is intended to refer to images that are larger or smaller than the original; and the act of "magnifying" refers to a "magnified" image and/or an image in the act of being magnified. For example, an image that is twice as large as the original is a "magnified" two-dimensional image; "magnifying" an image so that the image is much larger may be more conducive for using a far-field microscope to optically examine nanostructures. However, in another example, magnified images that are smaller than the original (e.g., the image is ten percent the size of the original) may be utilized for etching an image. It is envisioned that a structure may be magnified to produce a magnified two-dimensional image to etch the image, e.g., etching of nanostructures and/or for other uses. Additionally or alternatively, a magnified two-dimensional image may have distortions despite them not being desirable in all applications. For example, a magnified two-dimensional image may be warped, "out of focus", proportionality may be distorted, non-even, and/or may suffer from other types of changes that may occur when an image is magnified. However, there are several well known techniques to mitigate many of these anomalies.

Because of the metal surface roughness and the Raleigh scattering in the dielectric droplet 12 (the dotted line in FIG. 1(a) indicates the droplet's optical axis), the propagating plasmons are constantly scattered into normal photons propagating in free space. As a result, the plasmon-produced far-field two-dimensional image 18 on the metal surface 20 may be visualized by through a normal optical microscope objective 24. The image brightness far exceeds the background of scattered plasmons in other areas of the two-dimensional microscope, and in addition, a fluorescence scheme of surface plasmon field visualization by a far-field optical microscope may be used (see H. Ditlbacher, J. R. Krenn, G. Schider, A. Leitner, and F. R. Aussenegg, Two-dimensional optics with surface plasmon polaritons, *Appl. Phys. Letters*, vol. 81, pages 1762-1764, 2002).

The dielectric droplet 12 is preferably a glycerin droplet. However, any liquid dielectric droplet can be used in accordance with the present disclosure. Additionally, instead of using a liquid dielectric droplet, a solid parabolically shaped dielectric layer can be provided on the metal surface 20 and used as a lens and/or mirror for surface plasmons in accordance with the present disclosure.

The exact coupling efficiency between the plasmon-produced image 18 and photons in free space which may be collected by a regular microscope depends on the surface roughness and/or the type of fluorescent dye used in the microscope. A typical surface plasmon resonance linewidth measured in the experiment is in the 1-10% range (see H. Raether, *Surface Plasmons*, Springer Tracts in Modern Physics, vol. 111, Springer, Berlin, 1988), which indicates plasmon to photon conversion efficiency due to surface roughness of about the same order of magnitude. About the same conversion efficiency has been observed in the fluorescent imaging experiment (see Ditlbacher et al.). In addition, this coupling efficiency may be improved by introducing an artificial periodic corrugation of the metal surface (however, such an artificial surface corrugation may cause difficulties in distinguishing real objects from the patterns produced by periodic corrugation).

Thus, the goal of a two-dimensional microscope design is to have sufficiently high two-dimensional image magnification, so that all the two-dimensional image details would be larger than the $\lambda/2$ resolution limit of the normal optical microscope. As a result, a far-field optical microscope with nanometer-scale resolution is produced in accordance with the present disclosure and as described herein and reported in I. I. Smolyaninov, J. Elliott, A. V. Zayats, and C. C. Davis, Far-field optical microscope with nanometer-scale resolution, received by *Phys. Rev. Letters* on Mar. 10, 2004, the contents of which are incorporated herein by reference. Experimental proofs of the microscope's resolution of at least 50 nm, which is equal to approximately $\lambda/10$ and far supersedes resolution of any other known far-field optical microscope, have been demonstrated and presented. The microscopy technique in accordance with the present disclosure is believed will lead to numerous breakthroughs in biological imaging and sub-wavelength lithography.

However, the theoretical description of the microscope given above presents an oversimplified picture of the microscope operation. For example, the imaginary part of the metal's dielectric constant severely limits the shortest attainable surface plasmon wavelength and the surface-plasmon propagation length in most cases. This in turn limits the microscope's two-dimensional magnification in the metal plane. Herein is described how these limitations have been overcome in the experiment, and provide an analysis regarding the practical limits on the surface plasmon microscope resolution. In addition, experimental results are presented which strongly support the conclusion of extremely high spatial resolution of the surface plasmon microscope of the present disclosure.

III. Shortest Wavelength of a Surface Plasmon

The amplitude of every resonance in nature is limited by the energy losses. The same statement is valid with respect to the surface plasmon resonance. It is clear from eq. (1) that the imaginary part of $\epsilon_m(\omega)$ limits the shortest attainable wavelength of surface plasmons on an infinitely thick metal film. Given the assumption that $\epsilon_d$ is real, while $\epsilon_m = \epsilon^{(r)}_m + i\epsilon^{(i)}_m$, the shortest wavelength of a surface plasmon would be equal to $$\lambda_{Pmin} = \lambda \left( -\frac{2\epsilon_m^{(i)}}{\epsilon_d \epsilon_m^{(r)}} \right)^{1/2} \quad (3)$$

In the frequency range of the Ar-ion laser lines (which corresponds to the plasmon resonance at the gold-glycerin interface reported in I. I. Smolyaninov, J. Elliott, A. V. Zayats, and C. C. Davis, Far-field optical microscope with nanometer-scale resolution, received by *Phys. Rev. Letters* on Mar. 10, 2004) this value could not be much smaller then 200 nm. Thus, the idealized surface plasmon dispersion curve shown in FIG. 1(b) has nothing to do with reality if the gold film is very thick and glycerin is used as a dielectric.

However, the situation changes radically if the gold film thickness falls into the few tens of nanometers range, and the dielectric constant of the substrate used for the gold film is chosen to coincide with the dielectric constant of the liquid droplet on the gold film surface. In such a case, a pair of surface plasmon modes appears (the symmetric and the antisymmetric solutions of the Maxwell equations), and in the large wave vector limit the surface plasmon dispersion in eq.(1) is modified to look as follows:

$$k_p = \frac{\omega}{c} \left( \frac{\epsilon_d \epsilon_m}{\epsilon_d + \epsilon_m \pm 2\epsilon_d e^{-k_p d}} \right)^{1/2}, \quad (4)$$

where d is the gold film thickness. The term $2\epsilon_d e^{-k_p d}$ in the denominator of eq. (4) has real and imaginary parts, so that by playing with the frequency and the gold film thickness the plasmon momentum may be forced to diverge in the case of the antisymmetric plasmon mode (see J. J. Burke, G. I. Stegeman, and T. Tamir, Surface-polariton-like waves guided by thin, lossy metal films, *Phys. Rev. B*, vol. 33, pages 5186-5201, 1986.

Figure 1B:
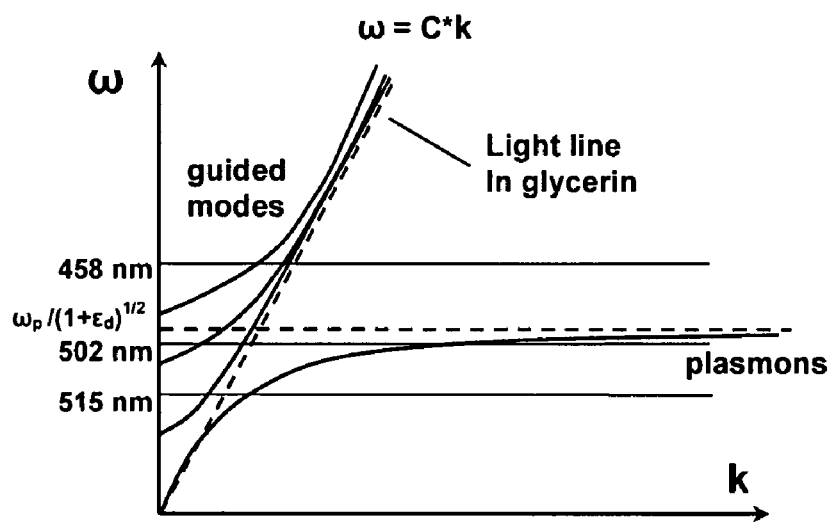
FIG. 1(b) is a graph illustrating Ar-ion laser line positions with respect to the dispersion curve of plasmons on the gold-glycerine interface shown in FIG. 1(a), and the approximate locations of other guided optical modes inside the thin layer of glycerine.

As a result, the use of an idealized surface plasmon dispersion curve shown in FIG. 1(b) is justified for a finite thickness of the gold film in a situation in which the dielectric constants of the droplet and the substrate are close to each other. Thus, glycerin with the refractive index of $n_{gl}=1.47$ is ideally suited for experiments performed with gold films deposited onto a glass substrate. It is noted that the use of materials with larger dielectric constants in the visible range (such as diamond or semiconductors) would improve the situation even for the thicker gold films (and make it more close to an ideal) since this would shift the plasmon resonance towards longer wavelengths where the $\epsilon^{(i)}_m$ falls very rapidly.

IV. Extending the Surface Plasmon Propagation Length

While the use of idealized surface plasmon dispersion curve in FIG. 1(b) for glycerin droplets has been justified in the previous section, even more crucial question for the consideration of the far-field surface plasmon microscope performance is the surface plasmon propagation length. The importance of this question may again be illustrated in the case of infinitely thick metal film. For a complex $\epsilon_m$ the imaginary part of $k_p$ from eq. (1) determines the surface plasmon propagation length $L_p$. Around $\lambda_{Pmin}$ the propagation length becomes extremely short: $L_p \sim 2\lambda_{Pmin}$, and it is clear that a far-field surface plasmon microscope could not be built in this case.

However, it appears that the use of symmetric geometry may again help to overcome the surface plasmon propagation problem. The effect of dramatic enhancement of the surface plasmon propagation length over a thin metal film in the symmetric configuration has been described previously by Burke et al. in J. J. Burke, G. I. Stegeman, and T. Tamir, Surface-polariton-like waves guided by thin, lossy metal films, *Phys. Rev. B*, vol. 33, pages 5186-5201, 1986. According to their calculations, the plasmon propagation over a symmetric structure appears to be typically an order of magnitude larger compared to the case of an asymmetric structure. For example, a surface plasmon propagation at $\lambda=633$ nm over a 15 nm thick silver film surrounded on both sides by a dielectric with refractive index 1.5 may reach 610 micrometers. Moreover, Burke et al. had found two additional leaky surface-plasmon-like solutions in the thin film geometry and noted that such leaky modes may even grow in intensity with distance under the resonant excitation if the rate of energy influx from the excitation source is greater than the dissipation in metal.

Here we should point out that in our experiments, as reported in I. I. Smolyaninov, J. Elliott, A. V. Zayats, and C. C. Davis, Far-field optical microscope with nanometer-scale resolution, received by *Phys. Rev. Letters* on Mar. 10, 2004, a substantial portion of surface plasmon propagation occurs over the areas of gold films which were perforated by the periodic arrays of nanoholes. It is clear that all the surface plasmon-like modes, which propagate over a periodically corrugated gold surface must be leaky modes due to the photonic crystal effects.

Figure 2:
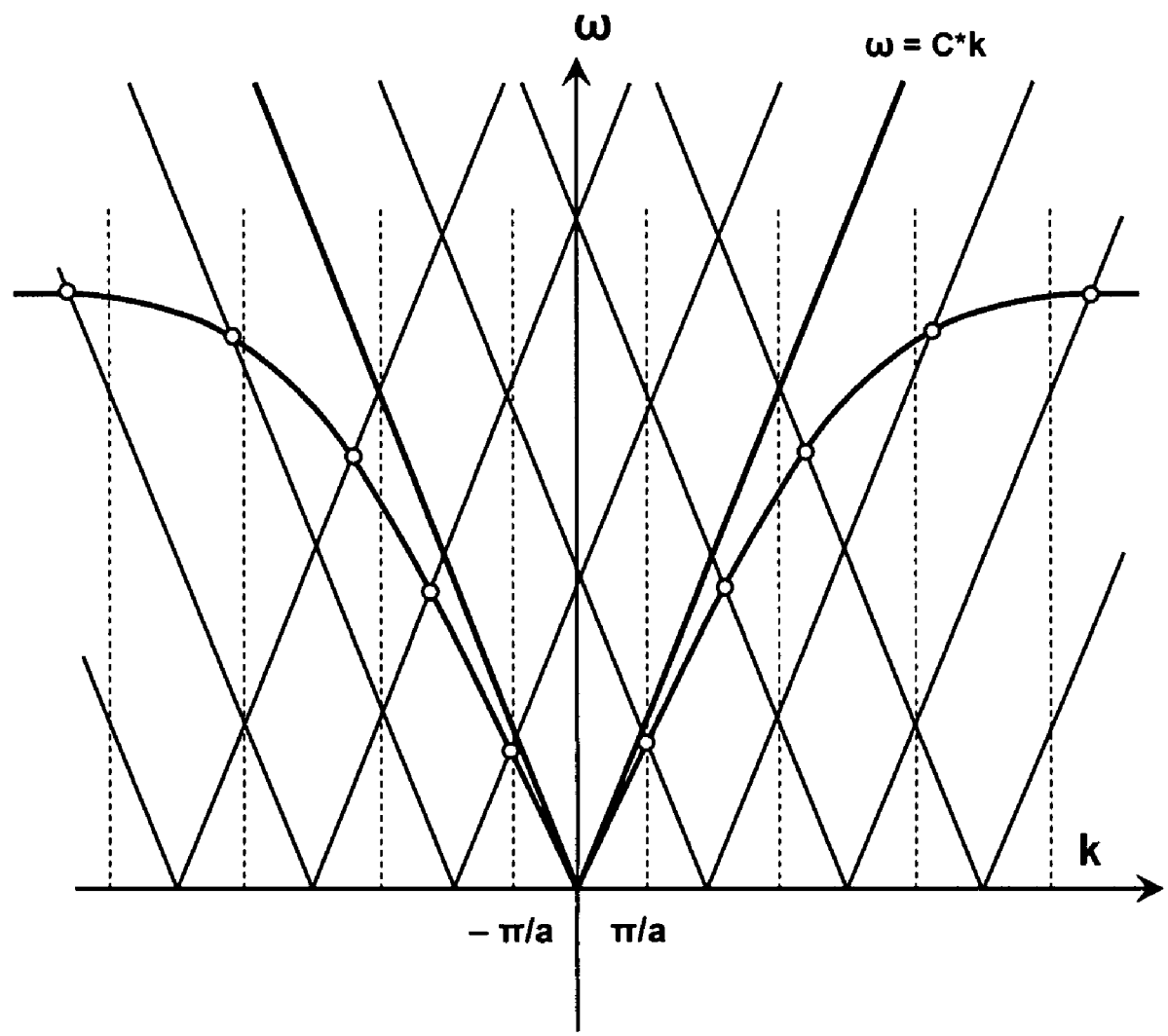
FIG. 2 illustrates the dispersion laws of surface plasmons and normal photons propagating inside the dielectric (shown in FIG. 1(a)) at small angles along the metal-dielectric interface, where the k-axis represents the quasi-momentum of the respective electromagnetic mode and the intersections between the modes are shown by the dots.

The dispersion laws of surface plasmons and normal photons propagating inside the dielectric at small angles along the metal-dielectric interface are shown in FIG. 2, where k represents the quasi-momentum of the respective electromagnetic mode. Since each branch (photon or plasmon) of the dispersion law can be shifted along the k-axis by an integer number of the inverse lattice vectors, it is clear that these branches have an infinite number of intersections with each other. These intersections are shown by the dots in FIG. 2.

Irrespective of the nature of the periodic corrugation (nanoholes like in our experiments, or something else), the propagation length of surface-plasmon-like modes drastically changes near these intersection points. According to the observation by Burke et al., plasmon propagation length near the intersection points between the dispersion laws of plasmon-like modes and photons in the dielectric should increase dramatically. The physical reason for this effect may be understood as though plasmons spend some of their lifetime as regular photons, and thus, propagate much farther. On the other hand, under the resonant excitation plasmon-like leaky modes which propagate over a periodic surface may even grow in intensity if the rate of energy influx from the excitation source is greater than the dissipation in metal. It is pointed out that the vast majority of the intersection points in FIG. 2 are located in the large wave vectors area of the unperturbed plasmon dispersion curve, which is exactly the property needed for high resolution microscopy. Thus, while the exact values of surface plasmon propagation length over a periodic nanohole array need to be calculated from the first principles, there exist good reasons for this propagation length to be large over the nanohole array for short-wavelength plasmons.

In order to achieve the best possible magnification of the plasmon microscope, both effects of the plasmon propagation length increase described above should be used: the preferred geometry of the two-dimensional microscope according to the present disclosure should be based on a thin periodically corrugated metal film surrounded on both sides by dielectric media with equal dielectric constants. The results of the measurements of surface plasmon propagation length shown in FIG. 3 and described in detail in Section VI confirm substantial increase of the surface plasmon propagation length in a symmetric configuration chosen in our experiments.

V. The Role of Mode Coupling

Liquid droplets with large-enough thickness may support not only the surface plasmons at the metal-dielectric interface but regular guided modes as well (FIG. 1(b)). These guided modes are similar to the electromagnetic modes that propagate in dielectric waveguides. The droplet profile changes with distance along its optical axis: ideally the droplet has a parabolic shape in the xy-plane, and in addition, the droplet thickness varies in the z-direction. Far from the droplet edges both the droplet thickness and the droplet width vary slowly, which leads to weak coupling between all the electromagnetic modes of the system due to momentum non-conservation (because of the loss of translation symmetry along the metal plane). This effect has been observed in our experiments (see FIG. 3(c, d) and detailed discussion in Section VI).

The diffraction-limited angular resolution $\sim\lambda_p/F$ of the microscope according to the present disclosure is defined by the plasmon propagation around the focal point of the parabolic mirror/droplet, where F is the focal length of the mirror and $\lambda_p$ is the plasmon wavelength. Once the short-wavelength surface plasmons left the area in the vicinity of the focal point, and reached some more distant area of the droplet with a larger width D>>F, plasmon conversion into the guided modes with larger wavelength $\lambda_g$ may not lead to the deterioration of the angular resolution (see the sketch in FIG. 3(e)). If $\lambda_p/F\sim\lambda_g/D$ angular resolution of the microscope will be conserved. After such a conversion, the two-dimensional image formed by the propagation of the guided modes will keep all the spatial information which would be contained in a plasmon-formed image if the plasmons would reach the geometrical location of the image. This statement is true as long as the geometrical optics description of the mode propagation inside the droplet remains valid, or if $\lambda_g<<F$. Thus, the mode coupling effect provides another way of solving the problem of short plasmon propagation length, which has been discussed in the previous section.

Based on the discussion above, the best shape of the dielectric droplet seems to be a compound shape, which may be approximated by two parabolas such that the focal length of the first parabola is much smaller than the focal length of the second one. In this case the role of the parameter D is played by the focal length of the second parabola, and the short-wavelength plasmons need to travel only a distance of the order of the focal length F of the first one. Such a compound droplet shape has been used in some of the experiments described below.

VI. New Experimental Evidence of Enhanced Resolution

In a scheme similar to one described in I. I. Smolyaninov, Surface plasmon toy-model of a rotating black hole, *New Journal of Physics*, vol. 5, pages 147.1-147.8, October 2003, glycerin microdroplets have been used as two-dimensional optical elements in the design of the plasmon microscope in accordance to the present disclosure. The dielectric constant of glycerin $\epsilon_g=2.161$ is ideally suited for experiments performed on a gold surface within the wavelength range of the laser lines of an argon-ion laser (FIG. 1(b)). At the $\lambda_0=502$ nm line, the real part of the gold dielectric constant is $\epsilon_m=-2.256$.

According to equation (1), the corresponding surface plasmon wavelength inside glycerin is $\lambda_p\sim70$ nm, and the effective refractive index of glycerin is $n_{eff}=\lambda_0/\lambda_p\sim7$. On the other hand, the use of glycerin achieves good dielectric constant matching with the silica glass, which has been used as a substrate for the gold films. According to the discussion above, this fact is important for improving surface plasmon propagation over the gold films with the thickness in the 50-100 nm range used in our experiments.

The plasmon propagation length over the gold-glycerin interface at 502 nm has been measured using two complementary techniques: near-field imaging technique described in I. I. Smolyaninov, Surface plasmon toy-model of a rotating black hole, *New Journal of Physics*, vol. 5, pages 147.1-147.8, October 2003 and Smolyaninov, I. I., Mazzoni, D. L., and Davis, C. C., Imaging of surface plasmon scattering by lithographically created individual surface defects, *Phys. Rev. Letters*, vol., 77, pages 3877-3880, 1996; and the fluorescent surface plasmon imaging technique similar to the one described in H. Ditlbacher, J. R. Krenn, G. Schider, A. Leitner, and F. R. Aussenegg, Two-dimensional optics with surface plasmon polaritons, *Appl. Phys. Letters*, vol. 81, pages 1762-1764. 2002. Both techniques gave similar results.

Figure 3B:
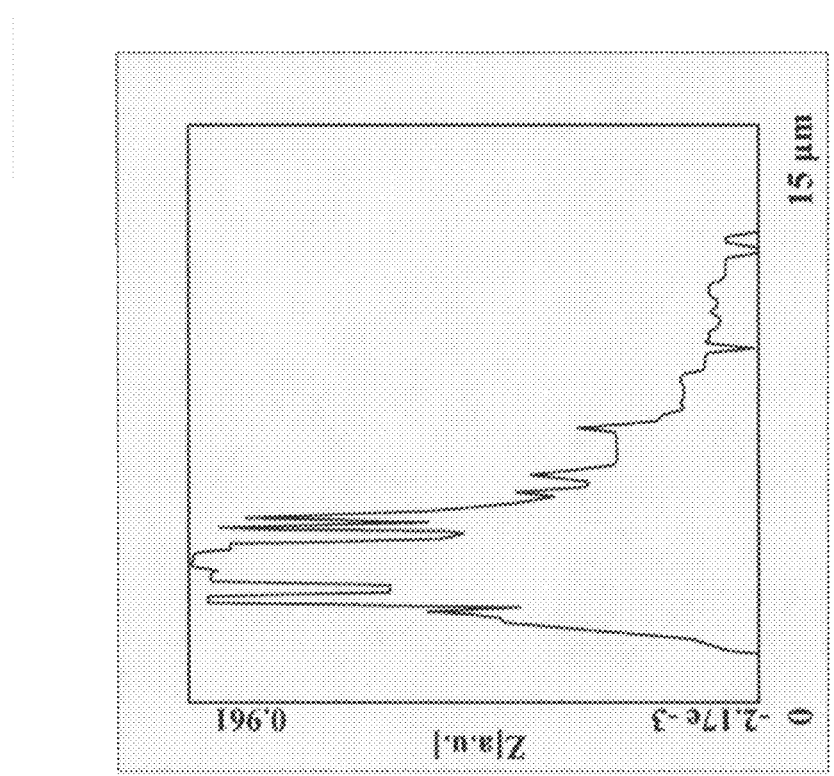
FIG. 3(b) is a graph illustrating a cross-section of the beam shown in FIG. 3(b)
Figure 3A:
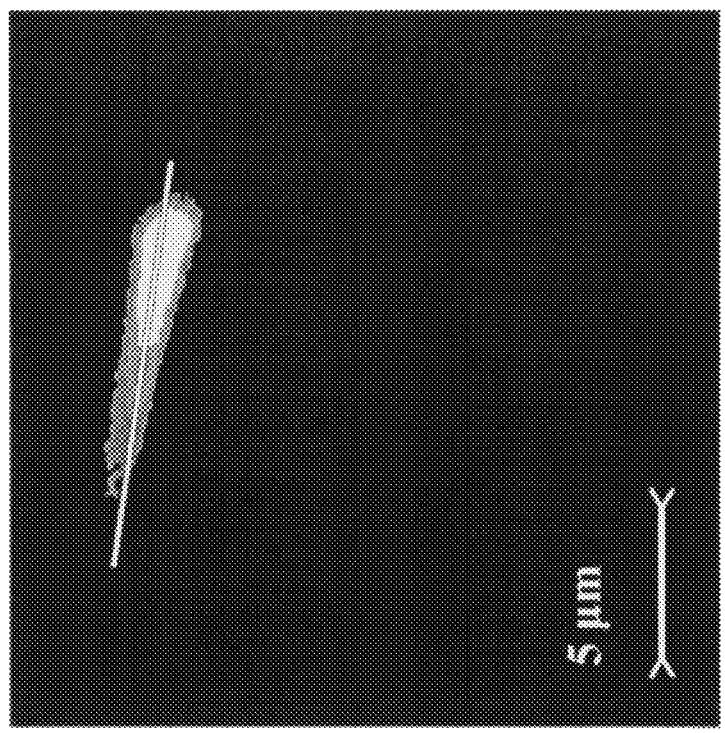
FIG. 3(a) illustrates an exponentially decaying surface plasmon beam emitted from an artificial pinhole in a 50 nm thick gold film immersed in a thin glycerin droplet stained with the bodipy die.
Figures 3C, 3D:
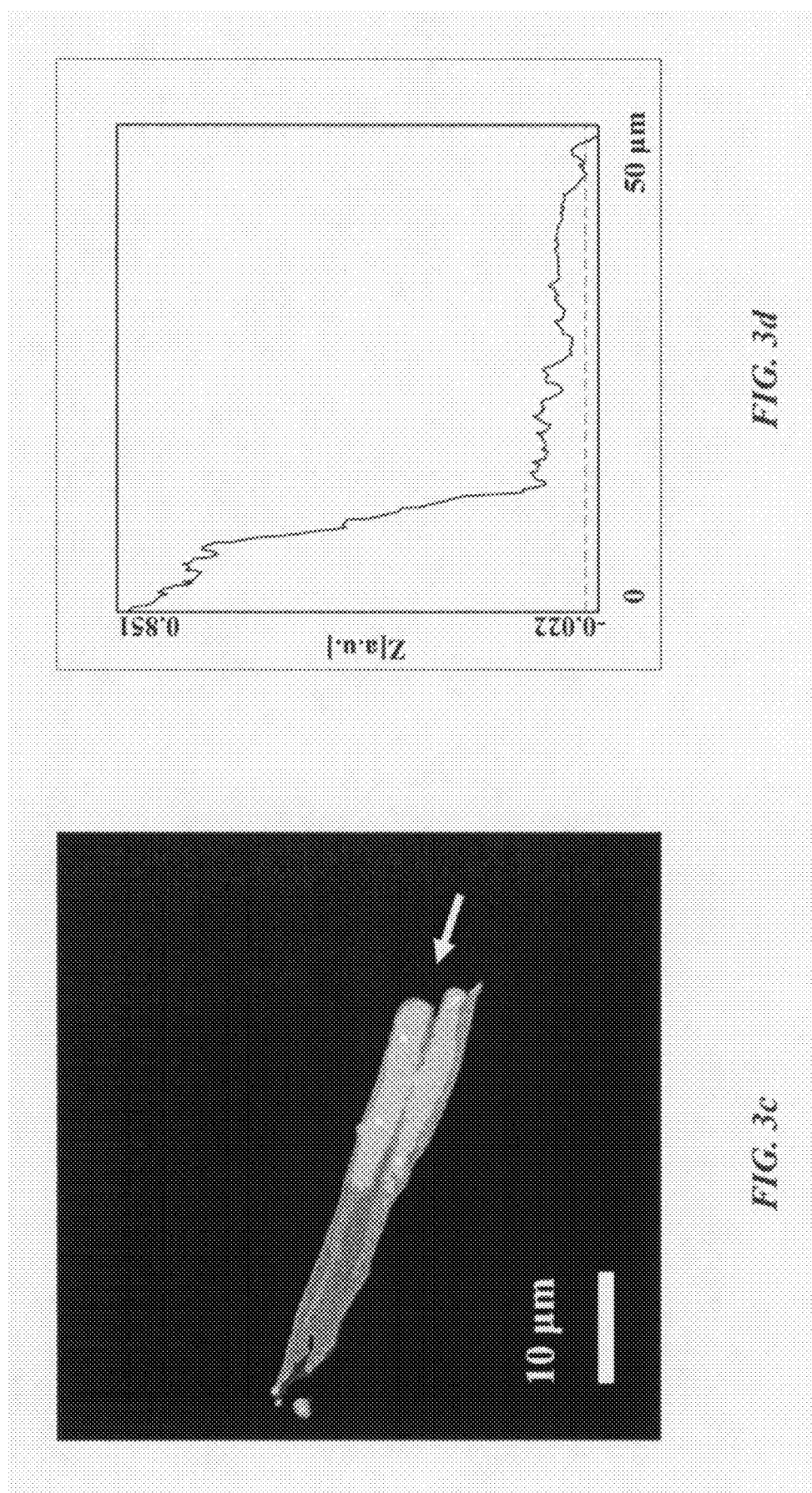
FIG. 3(c) illustrates an image undergoing the effect of mode coupling due to the slowly varying shape of the glycerin droplet, where quickly decaying surface plasmon beams emitted by two pinholes give rise to weaker guided mode beams, which exhibit much longer propagation length.
FIG. 3(d) is a graph illustrating a cross-section of the image shown in FIG. 3(c)

In our experiments artificial pinholes in gold film were produced inside a thin glycerin droplet (which was stained with the bodipy dye) by touching the gold film with a sharp STM tip. Such pinholes are known to emit propagating surface plasmon beams. The characteristic exponentially decaying surface plasmon beam (excited from the right side of the image) observed in this experiment is shown in FIG. 3(a), which has been obtained using fluorescent imaging. The cross-section of this beam shown in FIG. 3(b) has been fitted by an exponent and indicates plasmon propagation length of the order of 3 micrometers at 502 nm laser wavelength. In some cases it was possible to image the process of surface plasmon coupling into the regular guided modes described in Section V, as shown in FIGS. 3(c, d). Image (c) and its cross-section (d) show the effect of mode coupling due to the slowly varying shape of the glycerin droplet: quickly decaying surface plasmon beams emitted by two pinholes give rise to weaker guided mode beams, which exhibit much slower decay and longer propagation length.

Figure 4A:
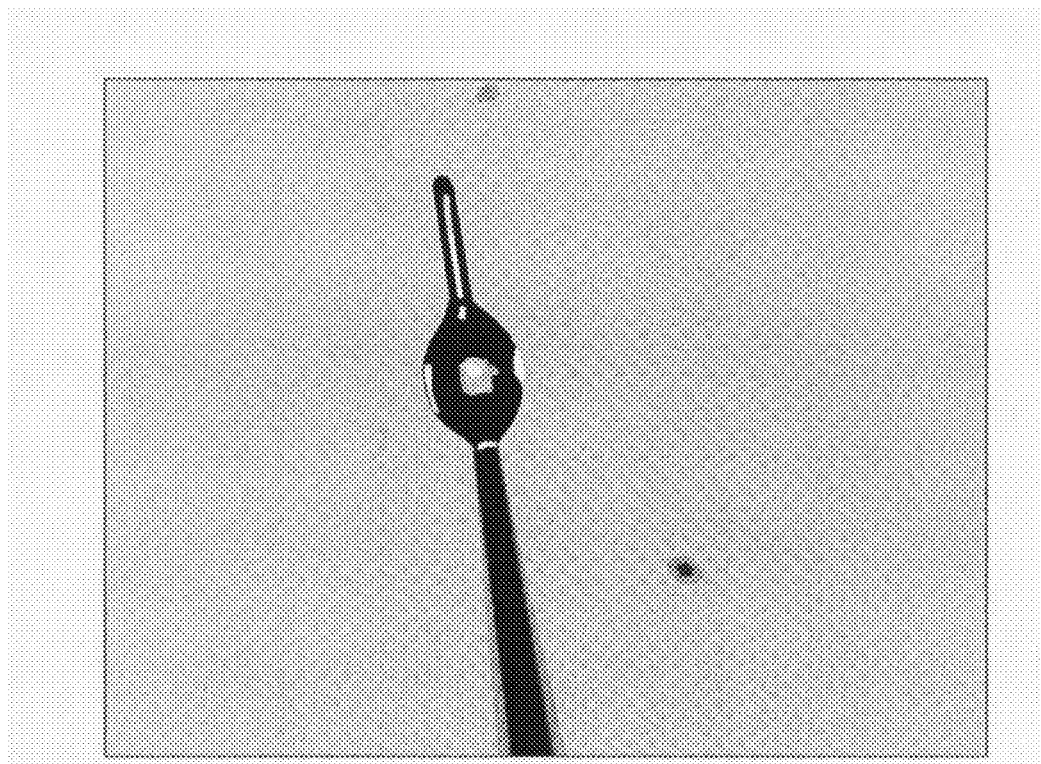
FIG. 4(a) is a photograph showing the formation of glycerin droplets in desired locations on the metal film by bringing a small probe wetted in glycerin into close proximity to a sample.
Figure 4B:
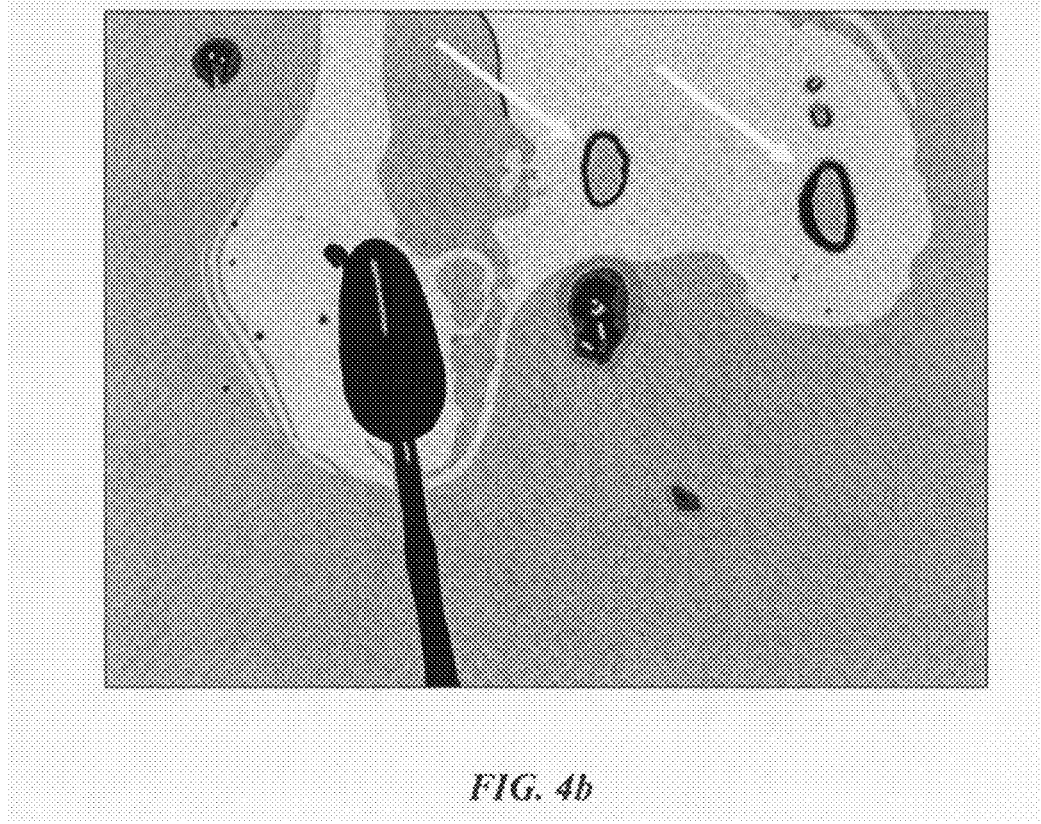
FIG. 4(b) is a photograph showing glycerin microdroplet formation in locations indicated by the arrows by bringing the probe to a surface region covered with glycerin.

In the microscopy experiments the samples were immersed inside glycerin droplets on the gold film surface. The droplets were formed in desired locations by bringing a small probe FIG. 4(a) wetted in glycerin into close proximity to a sample. The probe was prepared from a tapered optical fiber, which has an epoxy microdroplet near its apex. Bringing the probe to a surface region covered with glycerin led to a glycerin microdroplet formation under the probe (FIG. 4b). The size of the glycerin droplet was determined by the size of the seed droplet of epoxy. The glycerin droplet under the probe can be moved to a desired location under the visual control, using a regular microscope.

Our droplet deposition procedure allowed us to form droplet shapes, which were reasonably close to parabolic. In addition, the liquid droplet boundary may be expected to be rather smooth because of the surface tension, which is essential for the proper performance of the droplet boundary as a two-dimensional plasmon mirror. Thus, the droplet boundary was used as an efficient two-dimensional parabolic mirror for propagating surface plasmons excited inside the droplet by external laser illumination. Since the plasmon wavelength is much smaller than the droplet sizes, the image formation in such a mirror can be analyzed by simple geometrical optics in two dimensions.

Periodic nanohole arrays first studied by Ebbesen et al. (see T. W. Ebbesen, H. J. Lezec, H. F. Ghaemi, T. Thio, and P. A. Wolff, Extraordinary optical transmission through sub-wavelength hole arrays, Nature, vol. 391, pages 667-669, 1998) appear to be ideal test samples for the plasmon microscope of the present disclosure. Illuminated by laser light, such arrays produce propagating surface waves, which explains the anomalous transmission of such arrays at optical frequencies. FIG. 5 shows various degrees of two-dimensional image magnification obtained with a 30×30 $\mu m^2$ rectangular nanohole array with 500 nm hole spacing described in A. V. Zayats, I. I. Smolyaninov, W. Dickson, and C. C. Davis, Polarization superprism effect in surface polaritonic crystals, Appl. Phys. Letters vol. 83, pages 4438-4440, 2003 and used as a test sample.

In general, smaller glycerine droplets produced higher magnification in the images. It should be pointed out that all the guided modes in the droplet (surface plasmons and the regular guided modes shown in FIG. 1(b)) participate in the formation of the two-dimensional images. The relative contribution to the image of each mode changes with distance from the imaged sample due to varying mode coupling and decay. Approximate reconstructions of the images using two-dimensional geometrical optics (via ray tracing) are shown next to each experimental image. If the shape of the two-dimensional mirror (the droplet edge) is given by the exact parabolic dependence as $Y=X^2/2P$, the point $(X_1, Y_1)$ is reflected into the point $(X_2, Y_2)$ according to the following expressions:

$$x_2 = -\frac{P}{x_1}\left(\sqrt{\left(y_1 - \frac{P}{2}\right)^2 + x_1^2} - \left(y_1 - \frac{P}{2}\right)\right) \quad (5)$$

$$y_2 = \left(\frac{P^2}{2x_1^2} - \frac{1}{2}\right)\left(\sqrt{\left(y_1 - \frac{P}{2}\right)^2 + x_1^2} - \left(y_1 - \frac{P}{2}\right)\right) + \frac{P}{2} \quad (6)$$

These expressions are precise. However, the droplet shapes in our experiments may only approximately be represented by parabolas, and the damping of surface plasmon field over varying propagation lengths has not been included in the simulation (extensive sets of data on the plasmon propagation length versus the plasmon frequency and the metal and dielectric film thicknesses can be found in Burket et al.). These facts limit the precision of our image reconstructions.

Figure 5A:
FIGS. 5(a)-5(f) show images of a 30×30 μm² rectangular nanohole array with 500 nm hole spacing formed in various droplets.
Figure 5B:
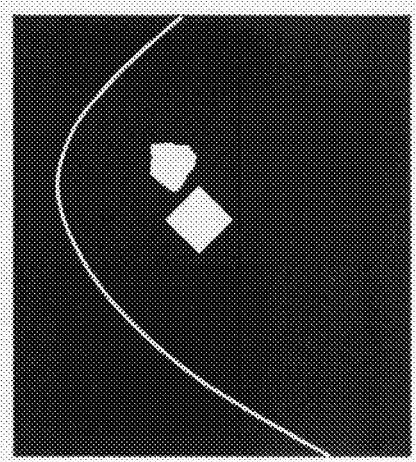
Figure 5C:
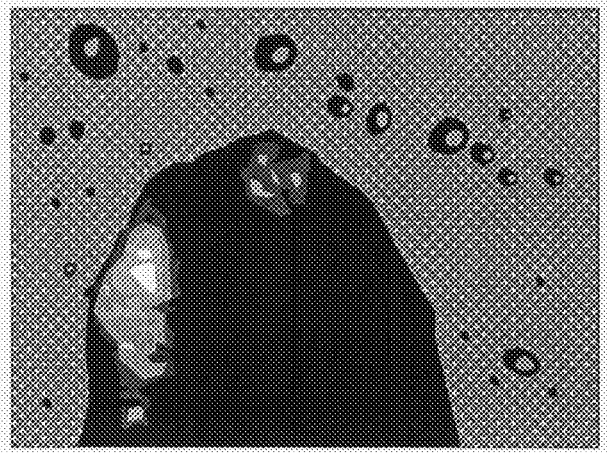
Figure 5D:
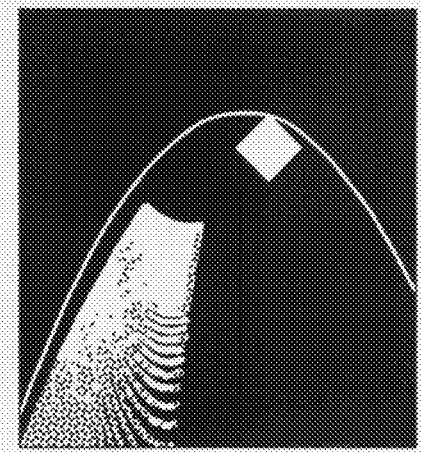
Figure 5E:
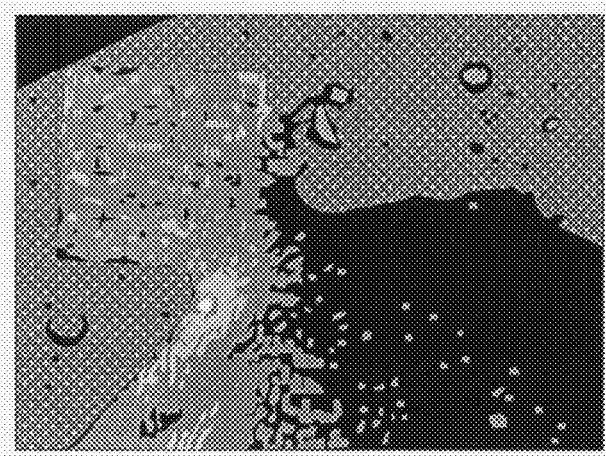
Figure 5F:
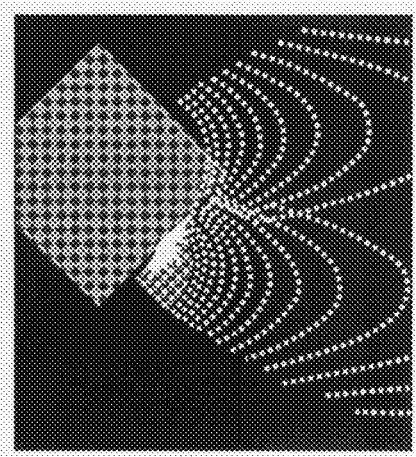

Nevertheless, we achieved a significant qualitative agreement between the experimental and theoretical images of the plasmon microscope according to the present disclosure. In all the calculated images described below the individual nanoholes of the arrays are shown as individual dots in the theoretical images. Comparison of FIG. 5(c) and FIG. 5(d) indicates that the rows of nanoholes separated by 0.5 µm may have been resolved in the image (c) obtained using only a 10× objective of the conventional microscope, while comparison of FIG. 5(e) and FIG. 5(f) obtained using a 50× objective indicates that individual 150 nm diameter nanoholes separated by 0.5 µm gaps are resolved in the image (e) obtained at 502 nm. These individual nanoholes are located in close proximity to the focus of the droplet/mirror, and hence experience the highest image magnification. In fact, the image in FIG. 5(e) shows successful use of the droplet with compound parabolic geometry described in the end of the previous section, which is supposed to take the full advantage of the mode coupling mechanism described in section V.

Even though the exact role of mode coupling in formation of each image in FIG. 5 is not clear, it seems certain that the two-dimensional images in FIGS. 5(a, c) are formed with considerable participation of the guided modes, since the distance travelled by the electromagnetic modes is of the order of 100 micrometers in these cases. While the image in FIG. 5(a) does not contain any evidence of high resolution, the image in FIG. 5(c) seems to demonstrate that the mode coupling does preserve high angular and spatial resolution, as has been discussed in section V.

Figure 6A:
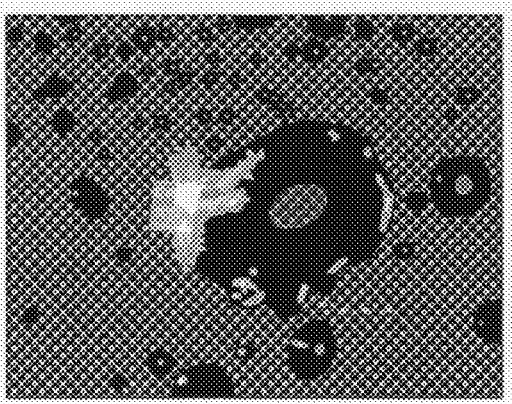
FIGS. 6(a)-6(f) show images of a resolution test of the microscope in accordance with the present disclosure.
Figure 6B:
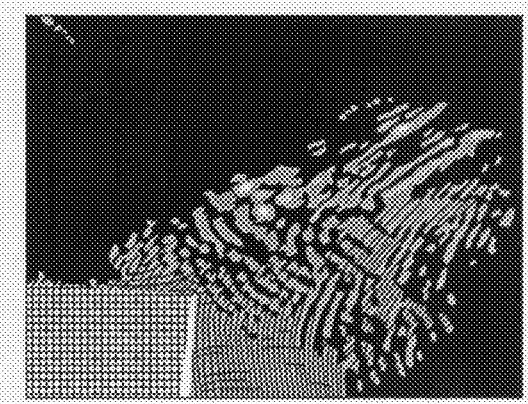
Figure 6C:
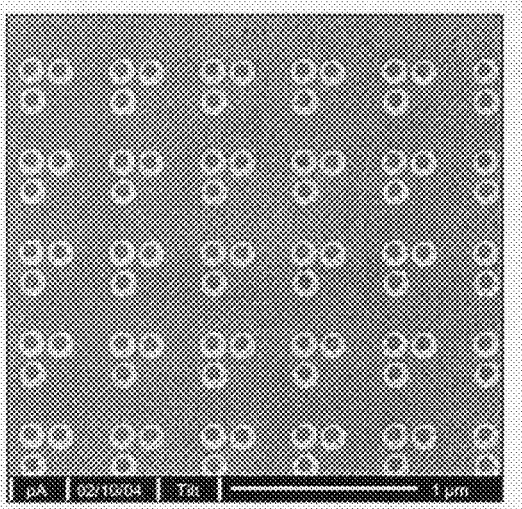
Figure 6D:
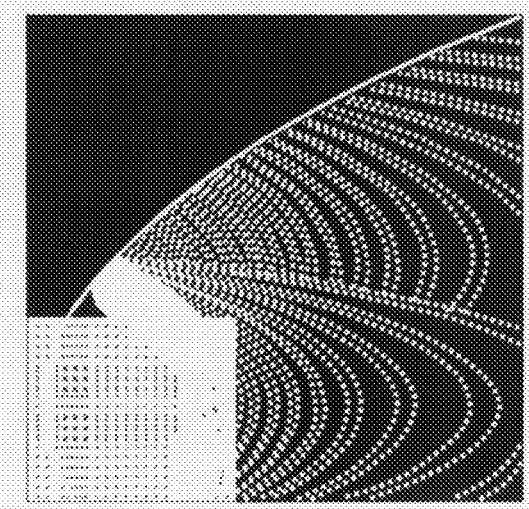
Figure 6E:
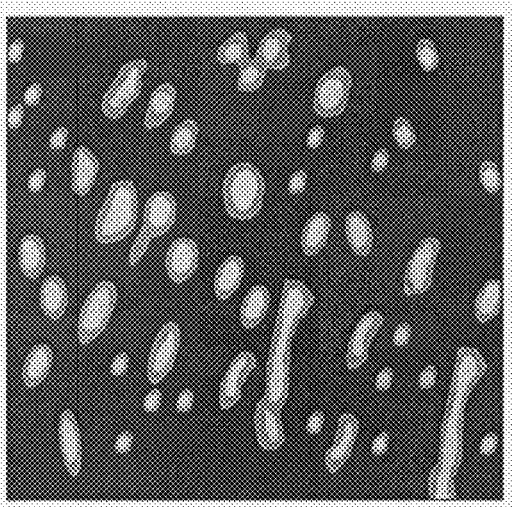
Figure 6F:
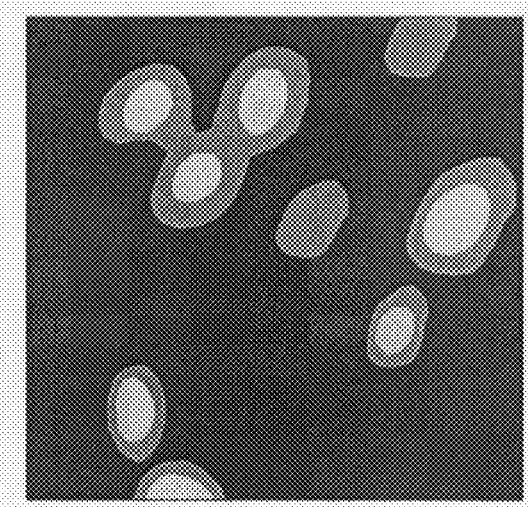

Another resolution test of the microscope of the present disclosure has been performed using a 30×30 µm$^2$ array of triplet nanoholes (100 nm hole diameter with 40 nm distance between the hole edges) shown in FIG. 6(c). This array was imaged using a glycerine droplet shown in FIG. 6(a). The image of the triplet array obtained at 515 nm using a 100× microscope objective is shown in FIG. 6(b) (compare it with an image in (d) calculated using the two-dimensional geometrical optics). Although the expected resolution of the microscope at 515 nm is somewhat lower than at 502 nm, the 515 nm laser line is brighter, which allowed for the obtainment of more contrast in the two-dimensional image. The least-distorted part of the image 6(b) (far from the droplet edge, yet close enough to the nanohole array, so that surface plasmon decay does not affect resolution) is shown at higher digital zooms of the CCD camera mounted onto a conventional optical microscope in FIGS. 6(e, f). These images clearly visualize the triplet nanohole structure of the sample.

Figure 7A:
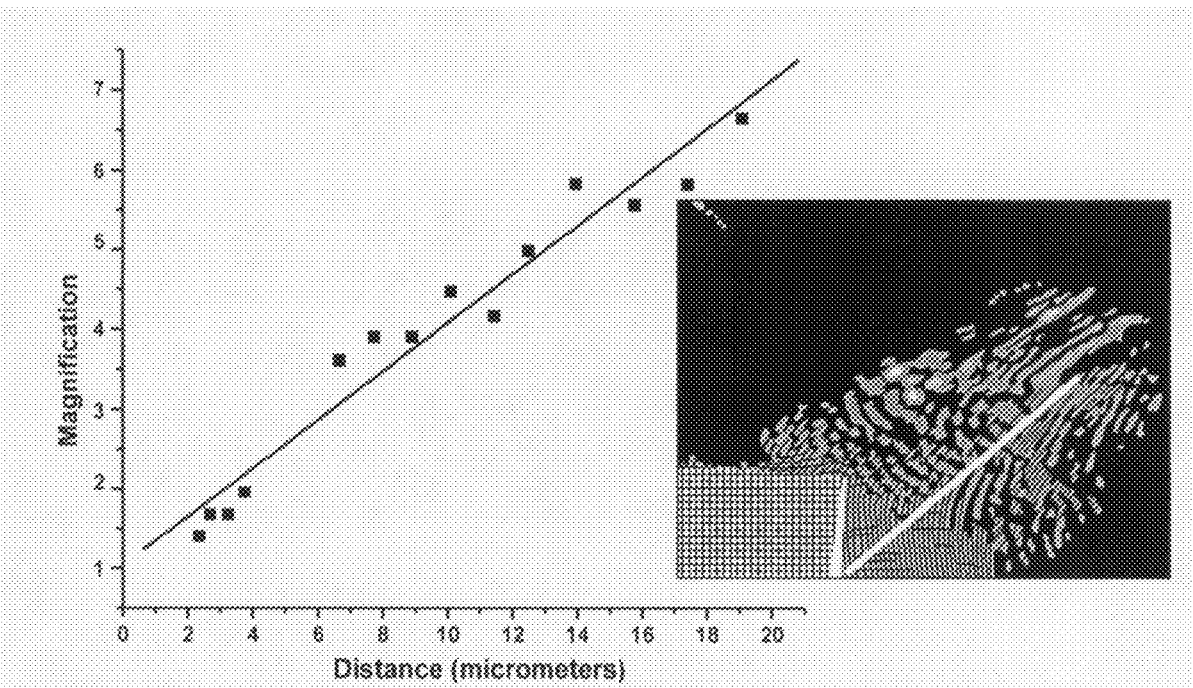
FIG. 7(a) is a graph illustrating image magnification measured in the surface plasmon image of a triplet nanohole array along the line shown in the inset, which is parallel to the optical axis of the droplet and where the dots in the graph show the distance between the neighbouring triplets in the image as a function of the triplet position measured along the optical axis.
Figure 7B:
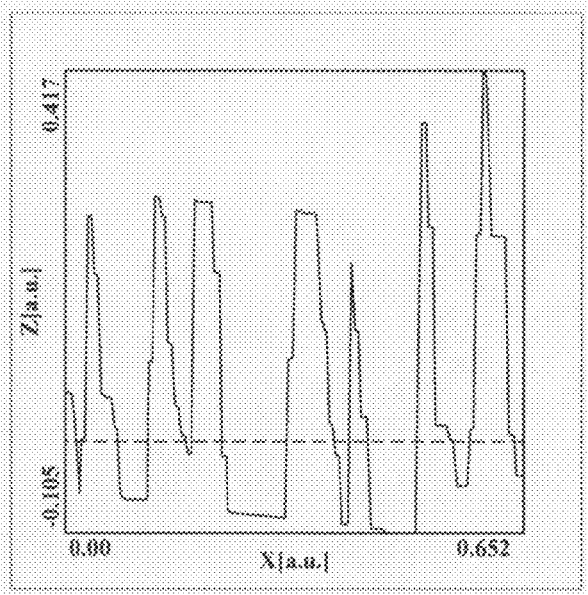
FIG. 7(b) is a chart illustrating the cross-section through the line of double holes in the image of the triplet nanohole array shown in FIG. 7(a)
Figure 8A:
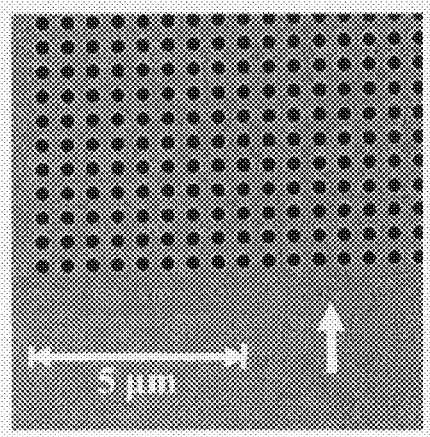
FIGS. 8(a) and 8(b) respectively illustrate electro microscope and plasmon microscope images of the gaps in the 30×30 μm² periodic nanohole array.
Figure 8B:
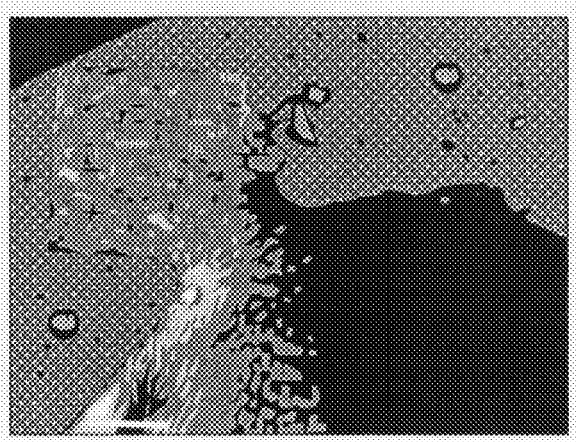
Figure 8C:
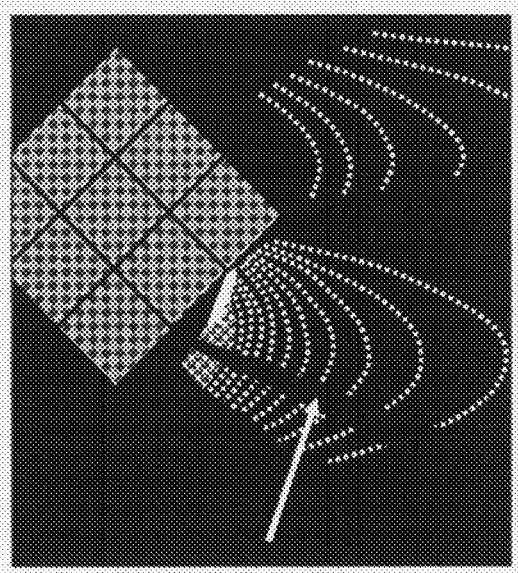
FIG. 8(c) is a schematic illustration of the theoretical ray-optics reconstruction of the image shown in FIG. 8(b)
Figure 8D:
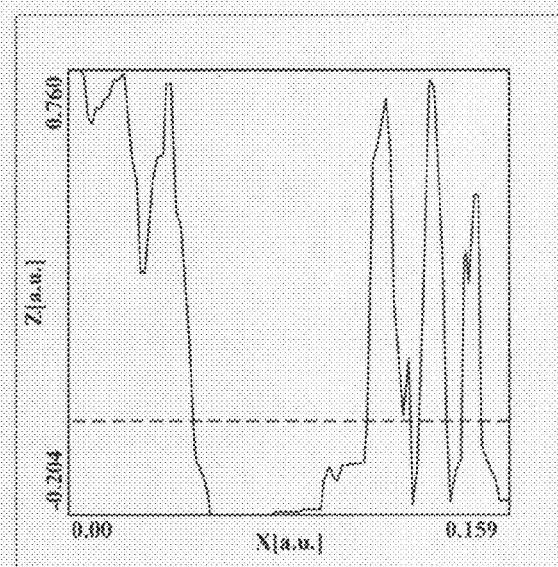
FIG. 8(d) is a graph illustrating a cross-section of the plasmon image obtained along the line shown in FIG. 8(b)
Figure 9A:
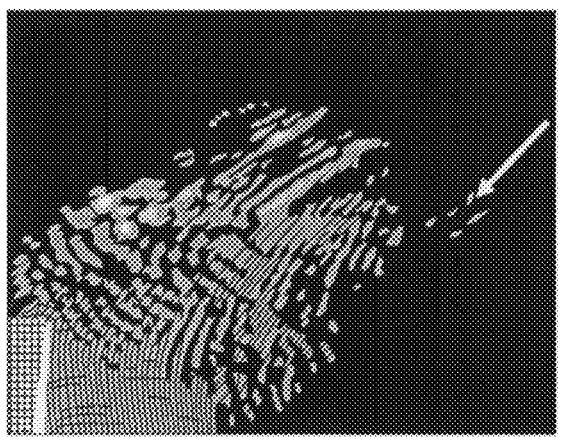
FIG. 9 illustrates images and data generated during an evaluation of the microscope designed in accordance with the present disclosure at a resolution of 502 nm.
Figure 9B:
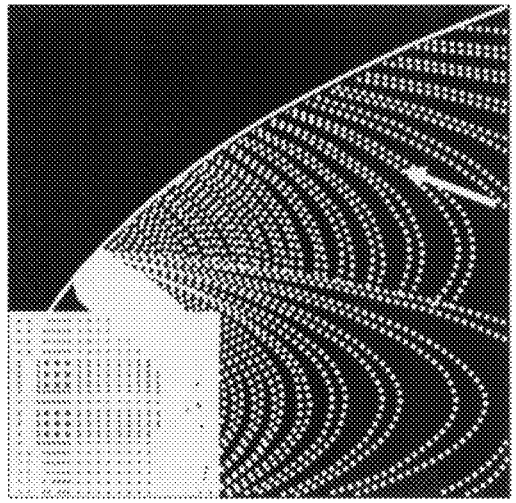
Figure 9C:
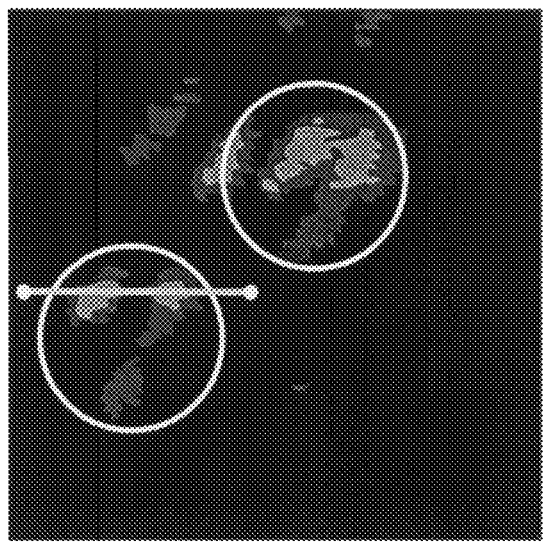
Figure 9D:
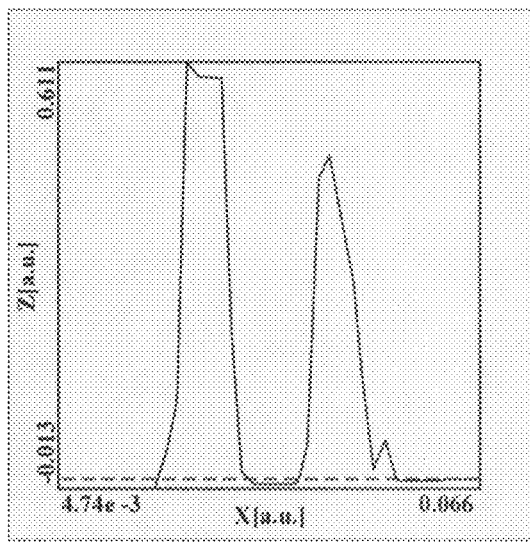

According to the geometrical optics picture of the two-dimensional plasmon microscope operation, its magnification M is supposed to grow linearly with distance along the optical axis of the droplet/mirror:

$$M = \frac{2y}{P} - 1, \quad (7)$$

where P is the focal distance of the parabola. Our measurements of the image magnification indeed exhibit such linear dependence (FIG. 7a). The dots in the graph show the distance between the neighbouring triplets in the image as a function of triplet position measured along the optical axis of the droplet. At small distances individual nanoholes are not resolved within the triplet. At larger distances (where the triplets are resolved, see the cross section in FIG. 7(b) measured through the line of double holes in the image of the triplet array, the data points represent the positions of the triplet's centres. The gap in the data corresponds to the intermediate area of the image in which the feature identification in the image is difficult. The slope of the measured linear dependence in FIG. 7(a) corresponds to P=7 µm, which is in reasonable agreement with the value of P of the order of 10 µm, which can be determined from the visible droplet dimensions in FIG. 6(a).

While the simple geometrical optics model of the image formation agrees reasonably well with the experiment, a few alternative mechanisms may form an image of a periodic source, such as the Talbot effect (see I. I. Smolyaninov, and C. C. Davis, On the nature of apparent "superresolution" in near-field optical microscopy, *Optics Letters,* vol. 23, pages 1346-1347, 1998). However, resolution of the Talbot images also approximately equals to λ/2n. Thus, whatever optical mechanism is involved in the formation of the images of the triplets in FIG. 6, short-wavelength plasmons are necessarily involved in this mechanism.

In addition, reconstruction of the source image in the Talbot effect happens at the specific planes where exact field distribution of the source is reproduced. These planes are called the Talbot planes. At all the distances, other then the set of Talbot distances, the pattern of illumination differs greatly from the pattern of the source: instead of triad features of the source, one may see sets of 6, 9, 12, etc. bright illumination maxima. This diffraction behavior is further complicated by the fact that different triads of the source are located at different distances from a given triad of the image. Since it is very hard to imagine that the periodicity of the source would exactly coincide with the periodicity of the Talbot planes spacing, the mechanism of image formation due to diffraction effects seems highly improbable. At the same time, all the diffraction and interference phenomena reproduce the geometrical optics description in the limit of small wavelengths. This fact is reflected in rather good agreement between the experimental images and the images calculated in the geometrical optics approximation.

In order to prove that the plasmon microscope is capable of aperiodic samples visualization, we have obtained images of small gaps in the periodic nanohole arrays (FIG. 8). The electron microscope image of one of the gaps in the periodic array of nanoholes is shown in FIG. 8(*a*). Two wider mutually orthogonal gaps were made in the array along both axis of the structure as shown in the theoretical reconstruction in FIG. 8(*c*). The plasmon image in FIG. 8(*b*) and its cross-section in FIG. 8(*d*) obtained at 502 nm wavelength shows both the periodic nanohole structure and the gap in the structure indicated by the arrows in the images. The width of the gap in the image grows linearly with the distance from the sample in agreement with the measurements in FIG. 7. In principle, the observed gap in the image might be interpreted as a Moire pattern, due to two shifted diffraction patterns from the two portions of the nanohole array separated by the gap.

However, the cross-section through the gap in the image (FIG. 8*d*) may be considered as evidence against such interpretation. Dark stripes in the Moire patterns normally exhibit slightly attenuated brightness compared to the original overlapping illumination patterns. The contrast in the image between the gap and the images of nanoholes seems to be too large for a Moire pattern interpretation.

Finally, in order to evaluate the microscope resolution at the optimized 502 nm wavelength, the cross-sections of the images of the triplet structure (similar to the one described earlier in FIG. 6) obtained at this wavelength were analyzed. The most magnified triplets, which are still discernible in the experimental image in FIG. 9(*a*) are shown by the arrow (compare this image with the theoretical one shown in FIG. 9(*b*)). These triplets are shown at a higher zoom in FIG. 9(*c*). The cross-section through two individual nanoholes in the triplet clearly shows the 40 nm gap between the nanoholes. While optical properties of this particular triplet may slightly differ from the designed values and lead to an appearance of a wider gap in the image, the distance between the centres of the nanoholes should be 140 nm. The cross-section in FIG. 9(*c*) seems to indicate at least three times better resolution of the plasmon microscope of about 50 nm. Thus, at least 50 nm (λ/10) spatial resolution of the microscope is clearly demonstrated. This high spatial resolution is consistent with the estimated 70 nm wavelength of surface plasmons at 502 nm.

Theoretical resolution of such microscope may reach the scale of a few nanometers, since only the Landau damping at plasmon wave vectors of the order of the Fermi momentum seams to be capable of limiting the smallest possible plasmon wavelength. However, increasing resolution may put additional extremely stringent requirements on the quality of the edge of the dielectric microdroplet/mirror used in the microscope and on the surface roughness of the metal substrate. In order to avoid image brightness loss due to plasmon scattering, the edge of the dielectric mirror should be smooth on a scale that is much smaller than the wavelength of the plasmons used. Surface tension of a viscous liquid mitigates this problem to some degree. However, enhancement of the optical resolution down to 10 nm scale may require novel technical solutions.

Nevertheless, the surface plasmon microscope in accordance with the present disclosure has the potential to become an invaluable tool in medical and biological imaging, where far-field optical imaging of individual viruses and DNA molecules may become a reality. It allows very simple, fast, robust and straightforward image acquisition. Water droplets on a metal surface could be used as elements of two-dimensional optics in measurements where aqueous environment is essential for biological studies (however, the use of water droplets may present some difficulties since change of dielectric media would require different matching conditions with the substrate, and water might not form equally parabolic and stable droplets as glycerin). It is also pointed out that if used in reverse, surface plasmon immersion microscope may be used in nanometer-scale optical lithography. Both of these developments would potentially revolutionize their respective fields.

VII. Conclusion

In conclusion, the present disclosure describes a far-field optical microscope capable of reaching nanometer-scale resolution using the in-plane image magnification by surface plasmon polaritons, also known as two-dimensional light, which is made of electromagnetic waves coupled with conducting electrons. The immersion microscope of the present disclosure improves resolution using an approach based on the optical properties of a metal-dielectric interface that may provide extremely large values of the effective refractive index $n_{eff}$ up to $10^3$ as seen by surface polaritons. Thus, the diffraction limited resolution can reach nanometer-scale values of $\lambda/2n_{eff}$. The experimental realization of such an immersion microscope has demonstrated the optical resolution better than 50 nm at 502 nm illumination wavelength.

The microscopy technique employed by the immersion microscope of the present disclosure improves resolution without expensive equipment and special preparations needed for electron microscopes and other technologies. The microscopy technique entails coaxing plasmon polaritons into magnifying images by placing a microscopic sample onto a thin, coated glass surface (such as a meta-coated glass surface that supports propagation of surface electromagnetic waves), like a document on the surface of a photocopier, and depositing a drop of glycerin or other substance on top of it. Alternatively, instead of depositing a drop of glycerin or other substance, a solid parabolically shaped dielectric layer can be provided on the metal surface. Laser light is then propagated or shined through the glass creating surface plasmon polaritons in the metal coating. The plasmon polaritons "sense" the sample by scattering off of it. They can sense finer details than ordinary light because their wavelength is only 70 nm, seven times shorter than that of the laser.

To concentrate the scattered two-dimensional light, the curved vertical surface 26 (see FIG. 1(*a*)) of the glycerin drop 12 where the light 16 contacts the metallic plane 28 and reflects plasmon polaritons is used. This vertical surface 26 (metal-dielectric interface) works a bit like a giant radio telescope dish in reverse: rather than focusing parallel astronomical light rays to a point, it collects the scattered plasmon polaritons emerging from the sample 14 and redirects them into a plasmon beam along the metallic plane 28. To view the image, nanoscale irregularities in the metal surface scatter some of the light of the beam upward, so that an ordinary microscope objective 24 can catch the image and be viewed through at least one lens 30 of the microscope positioned for viewing the image propagated by the scattered beam. The droplet's shape is adjusted "by hand" using micromanipulators, such as a probe. It is envisioned to replace this step with solid mirrors etched on the glass by lithography.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A surface plasmon polariton planar waveguide comprising:
    a planar surface configured to propagate the surface plasmon polaritons; and
    a parabolic structure disposed on the planar surface and having a first end for coupling an electromagnetic wave within the parabolic structure; at least one sidewall extending from the first end for internally reflecting the electromagnetic wave within the parabolic structure; and a second end providing a focal point for focusing the internally reflected electromagnetic wave thereat.

2. The planar waveguide according to claim 1, wherein the planar surface includes a metallic layer.

3. The planar waveguide according to claim 1, wherein the planar waveguide includes at least one dielectric material layer.

4. The planar waveguide according to claim 1, wherein the at least one sidewall of the parabolic structure extends vertically from the planar surface defining a vertical surface.

5. The planar waveguide according to claim 4, wherein the vertical surface collects scattered plasmon polaritons emerging from a sample disposed on the planar surface and redirects them into a plasmon beam along a plane of the planar surface.

6. The planar waveguide according to claim 5, wherein the planar surface includes nanoscale irregularities which scatter the plasmon beam.

7. The planar waveguide according to claim 5, wherein the wavelength of the plasmon polaritons is 70 nm.

8. The planar waveguide according to claim 1, wherein the parabolic structure is etched on the planar surface.

9. The planar waveguide according to claim 1, the planar surface comprising:
    a periodically corrugated metal film defining first and second sides;
    a first dielectric media film at least partially disposed on the first side of the periodically corrugated metal file, wherein the dielectric media film has a first dielectric constant; and
    a second dielectric media film at least partially disposed on the second side of the periodically corrugated metal film, wherein the second dielectric media film has a second dielectric constant approximately equal to the first dielectric constant.

* * * * *